US006969767B1

(12) United States Patent  
Bayod Jasanada et al.

(10) Patent No.: US 6,969,767 B1  
(45) Date of Patent: Nov. 29, 2005

(54) OPTICALLY ACTIVE CARBONATES AS PRECURSORS OF (+)-ZOPICLONE

(75) Inventors: Miguel Bayod Jasanada, Llanera (ES); Victor M. Sanchez Pedregal, Llanera (ES); Vicente Gotor Santamaria, Oviedo (ES); M. Rosario Brieva Collado, Oviedo (ES); Laura Fernandez Solares, Oviedo (ES); Monica Diaz Sierra, Oviedo (ES); Jose Manuel Guisan Seijas, Oviedo (ES); Jose Miguel Palomo Carmona, Oviedo (ES); Roberto Fernandez-Lafuente, Oviedo (ES)

(73) Assignees: Universidad de Oviedo, Oviedo (ES); Astur Pharma, S.A., Oviedo (ES)

( * ) Notice: Subject to any disclaimer, the term of this patent is extended or adjusted under 35 U.S.C. 154(b) by 40 days.

(21) Appl. No.: 10/405,998

(22) Filed: Apr. 2, 2003

(30) Foreign Application Priority Data

Apr. 3, 2002 (ES) ................................ 200200771

(51) Int. Cl.[7] .......................................... C07D 239/02
(52) U.S. Cl. ..................................................... 544/350
(58) Field of Search ........................................ 544/350

(56) References Cited

U.S. PATENT DOCUMENTS 3,862,149 A * 1/1975 Cotrel et al. .......... 260/268 BQ

FOREIGN PATENT DOCUMENTS

ES 2 101 653 * 1/1997

OTHER PUBLICATIONS

The Merck Index 13th ed. © 2001 MERCK & CO., INC. Whitehouse Station NJ, pp. 581 and 1426.*  
Gotor et al, "Enzymatic resolution of (+/−)-6-(5-chloropyridin-2-yl)-7-vinyloxy-carbonyloxy-6,7-dihydro [5H]pyrrolo[3,4-b]pyrazine 5-one. Synthesis of (+)-zopiclone" Tetrahedron: Asymmetry, vol. 8(7), pp. 995-997 (1997).*  
Jaeger and Eggert, "Lipases for biotechnology" Current Opinion in Biotechnology, vol. 13(4), pp. 390-397 (2002).*  
Sharma et al, "Production, purification, characterization, and applications of lipases" Biotechnology Advances, vol. 19, pp. 627-662 (2001).*  
Palomo et al, Tetrahedron Asymmetry, vol. 14, pp. 429-438 (2003).*

* cited by examiner

*Primary Examiner*—James O. Wilson  
*Assistant Examiner*—Zachary C. Tucker  
(74) *Attorney, Agent, or Firm*—Michaelson & Associates; Peter L. Michaelson; Edward M. Fink

(57) ABSTRACT

In the present invention new compounds of formula II, in enantiomerically enriched forms, are described for the first time, where $R^1$ is chloroalkyl. The present invention also includes several new enzymatic processes for the resolution of the enantiomers of the aforementioned carbonates of formula II from the corresponding racemic mixture. The transformation of these carbonates into zopiclone enantiomerically enriched, constitutes an additional aspect of the invention.

18 Claims, 2 Drawing Sheets

OPTICALLY ACTIVE CARBONATES AS PRECURSORS OF (+)-ZOPICLONE

Zopiclone is a cyclopyrrolone with hypnotic activity. Although the molecule, zopiclone, possesses a chiral centre up till now it is commercialised as the racemic mixture. Recent studies (*Chirality*, 1993, 5, 419) have confirmed that the dextrorotatory enantiomer is approximately twice as active as the racemate whereas the levorotatory isomer is almost inactive. Moreover, according to the EP patent 609210-B1 the levorotatory isomer is responsible for the majority of the adverse effects which are associated with the administration of the medicine. Therefore, it is much more convenient to use the optically pure S enantiomer than the racemate.

The present invention describes new optically active intermediates together with the enzymatic processes for their synthesis and their transformation in (+)-zopiclone.

PRIOR ART

Racemic zopiclone (I) was described for the first time, together with its synthesis from carbonates of formula II ($R^1$=phenyl optionally substituted), in U.S. Pat. No. 3,862,149. These carbonates are, in turn, obtained by means of the conventional reaction of the alcohol of formula III with a chloroformiate of formula Cl—CO—OR$^1$. (FIG. 1).

The enantiomers of zopiclone can be separated by crystallisation of the corresponding diastereoisomer salts obtained with optically active acids. For example, (+)- or (−)-malic acid (*Chirality*, 1993, 5, 419), or (+)-O,O'-dibenzoyltartaric acid (EP patent 609210-B1) can be used as chiral acids. The enantiomers may be also separated by chiral-phase chromatography.

In *Tetrahedron: Asymm.*, 1997, 8, 995 and in ES patent 2101653 the preparation of (+)-zopiclone is described, by means of synthesis from an optically active carbonate of formula II (with $R^1$=vinyl), in turn, obtained by means of the enzymatic resolution of a racemic mixture. As catalyst a commercial preparation of *Candida antarctica* lipase B immobilized on a solid support is used. The enzyme catalyses the reaction of said carbonate with a molecule of water, transforming preferably the enantiomer (−)-II. When 50% of conversion is reached the enantiomer (−)-II is practically consumed whereas the isomer (+)-II remains almost intact. Then the reaction is stopped and compound (+)-II is purified to be later converted into (+)-zopiclone. This enzymatic reaction can be performed in several anhydrous organic solvents. However, the process is limited to the vinyl carbonate ($R^1$=vinyl in the formula II) since the rest of the carbonates described in the aforementioned paper ($R^1$=ethyl, 2,2,2-trichloroethyl, benzyl and phenyl, in the formula II) do not react in the presence of the enzyme. Once the enantiopure carbonate II is obtained, it is converted in (+) zopiclone by means of reaction with N-methylpiperazine. The yield of this last step of the synthesis is a bit low; this fact together with the high cost of the vinyl chloroformiate makes the cost of the process high.

Another improvable aspect from the process described in ES patent 2101653, that is showed when the process is scale-up, is that the enzymatic catalyst utilized is easily physically degraded. Fortunately there are alternative methods of lipase immobilization on different solid supports. For instance in the WO patent application 99/51726-A the immobilization of lipases on highly hydrophobic supports is described, achieving in only one step the immobilization, purification, hyper activation and stabilization of the catalyst. Moreover these supports are resistant to the mechanical and chemical reaction conditions in aqueous media what makes possible the regeneration and reutilization of the catalyst. Also it is possible to immobilise the enzymes by other methods, such as trapping, ionic adsorption or covalent bounding.

A racemic mixture or a racemic compound is an equimolecular or practically equimolecular mixture of the two enantiomers of a given compound. It is said that a compound is optically enriched or enantiomerically enriched when one of the enantiomers is in greater ratio than the other, specially if the ratio of one of them is much greater than the other, specially is the ratio is 90:10 or higher.

DESCRIPTION OF THE INVENTION

In the preset invention new compounds of formula II, both in racemic and in enantiomerically enriched forms, are described for the first time, where $R^1$ is alkyl, alkenyl, aralkyl, aryl or succinimidyl, optionally ramificated and optionally substituted by one or several hetero atoms.

The present invention also includes several new enzymatic processes for the resolution of the enantiomers of the aforementioned carbonates of formula II from the corresponding racemic mixture.

Figure 1:
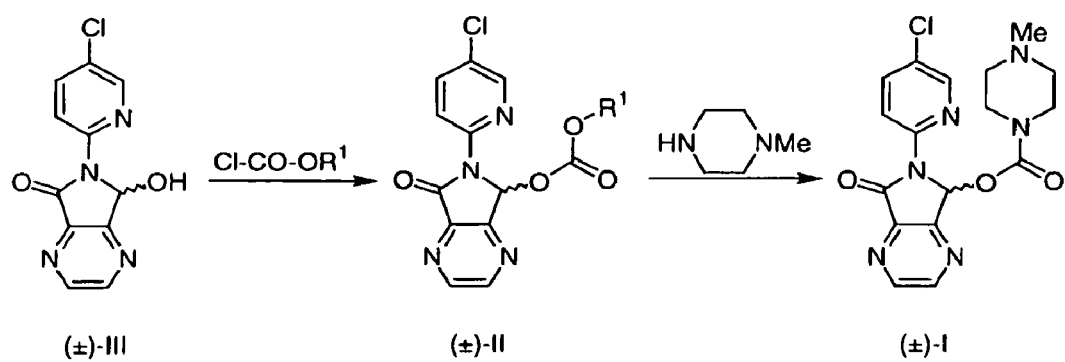
FIG. 1 illustrates the synthesis of racemic zopiclone (±-I) from carbonates of formula II obtained by reaction of the alcohol of formula III with a chloroformiate of formula Cl—CO—OR$^1$ and FIG. 2 illustrates the preparation of optically enriched (S)-Zopiclone by synthesis from an optically active carbonate of formula II obtained by the enzymatic resolution of the corresponding racemic mixture.
Figure 2:
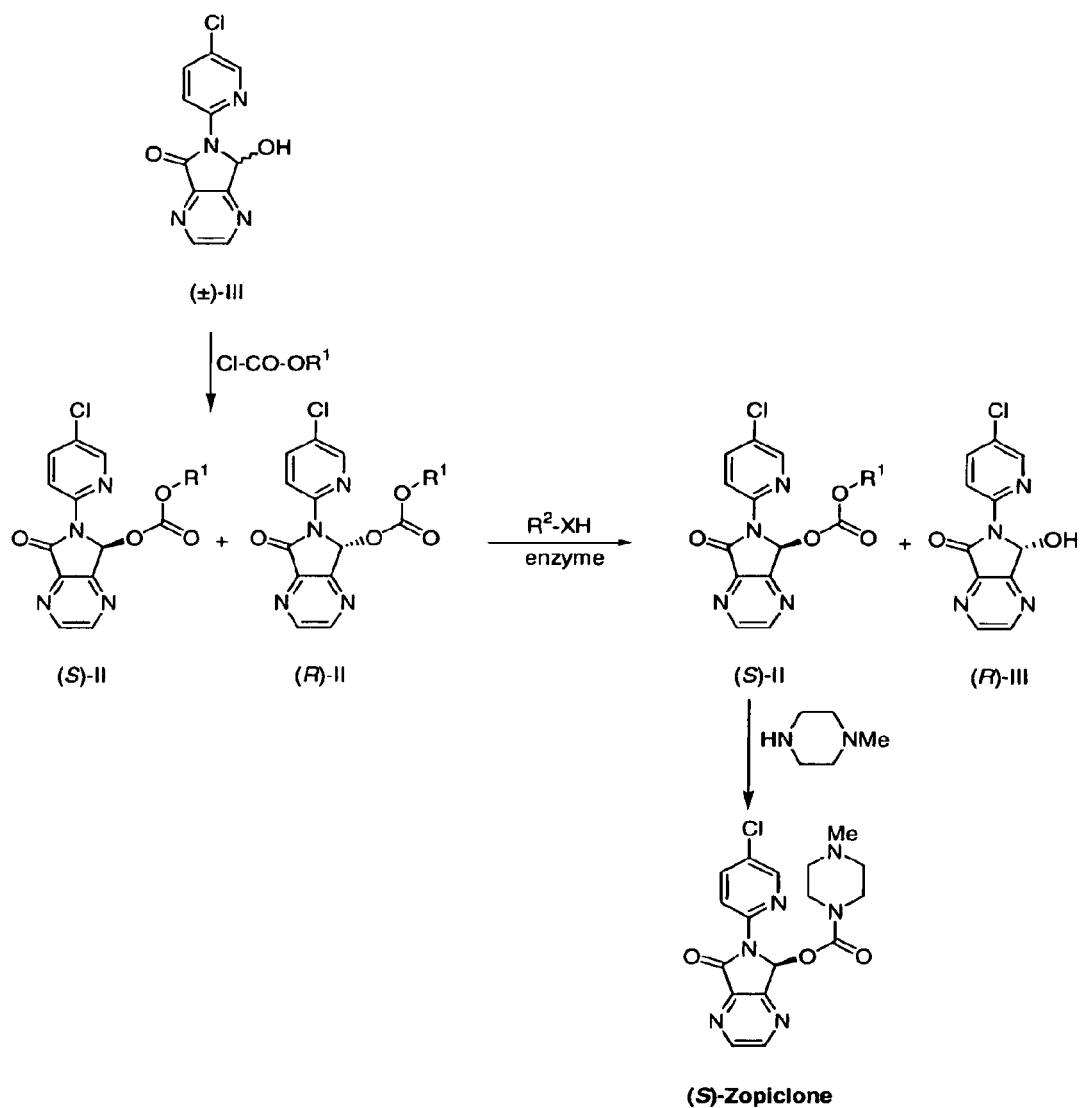

The transformation of these carbonates into zopiclone, both in racemic and enantiomerically enriched forms, constitutes an additional aspect of the invention (FIG. 2).

Finally, another aspect of the invention is the use of certain immobilized preparations of enzymes that are stable and active when big amount of co-solvent in aqueous medium is used.

In general, carbonates of formula II may be prepared from the alcohol of formula III and the corresponding chloroforminate Cl—CO—OR$^1$. The reaction is generally performed either in a basic solvent, for example pyridine, or in a neutral solvent to which a base is added. When $R^1$ is succinimidyl the N,N'-disuccinimidyl carbonate is used instead of the chloroformiate one.

The enantiomerically enriched carbonates are obtained from the corresponding racemic mixtures by kinetic resolution catalysed using an appropriate enzyme. The enzyme catalyses the reaction of the aforementioned carbonate with a molecule of water, of alcohol or other appropriate nucleophile, transforming preferably the enantiomer (−)-II. The reaction of this isomer affords the alcohol III and other by-products that are described later. In this way, as the conversion increases, the enantiomer (−)-II is consumed whereas the enantiomer (+)-II remains practically intact. When a certain value of conversion is reached practically all enantiomer (−)-II has been consumed and therefore isomer (+)-II remains practically enantiopure. The necessary conversion to reach this point depends on the enantioselectivity of the enzyme for each specific case. When the process is very enantioselective the compound (+)-II is obtained with high enantiomeric excess at conversions close to 50%. If the process is less enantioselective higher conversions are necessary to reach high enantiomeric excesses. The specific value of conversion at which the reaction should be stopped will depend on the enantioselectivity of each specific case and the optical purity requirements of the products. Said value is determined by a known method by an expert in the matter, as described, for example, in *J. Amer. Chem. Soc.* 1982, 104, 7294. Once the desired conversion is reached the reaction is stopped, for example, by filtering the enzyme.

Then, the remained compound (II) is purified by separation from compound III generated in the reaction. This separation can be performed by any convenient method, for example, by precipitation or chromatography. Depending on the specific reaction conditions, the compound III may precipitate in the reaction media as it is generated what facilitates its separation by filtration.

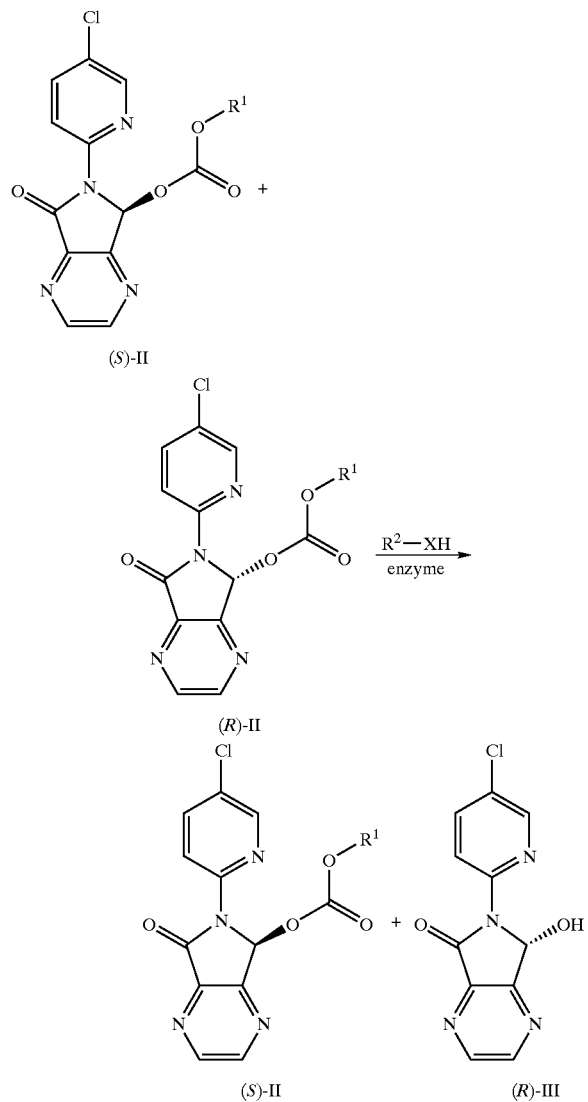

An unexpected aspect of the process is that the compound (R)-III, generated during the enzymatic resolution, undergoes spontaneous racemization in the reaction conditions, so, once it is purified, it can be directly used to produce more racemic carbonate of formula II. In this way all the raw material is usable and the amount of residual material is reduced.

The enzymatic resolution is performed preferably in an anhydrous organic solvent to which an appropriate amount of nucleophile (water, an alcohol, a phenol or a thiol, among others) is added. Theoretically, an equimolecular amount of nucleophile is sufficient, but it is often beneficial the use of and excess of 2:1, 3:1 or even higher. Examples of alcohols that may be used are: methanol, ethanol, isopropanol, butanol, benzyl alcohol, 1-phenylethanol, phenol or p-nitrophenol, among others.

When the nucleophile is an alcohol of formula $R^2$—OH for each molecule of formula II that reacts, a molecule of formula III and one of carbonate of formula $R^2$—O—CO—O—$R^1$ are released. The said carbonate, in turn, may react with another molecule of alcohol $R^2$—OH to give other carbonate of formula $R^2$—O—CO—O—$R^2$ and a molecule of alcohol $R^1$—OH, or it may react with another molecule of alcohol $R^1$—OH to give other carbonate of formula $R^1$—O—CO—O—$R^1$. When the nucleophile is water, the hydrolysis of the compound of formula II gives a molecule of the compound of formule III, and a molecule of alcohol of formula $R^1$—OH. This, in turn, can remain as it is in the reaction medium or can be converted in other by-products. It can also happen that the alcohol $R^1$—OH released acts as nucleophile in competition against the water; in this case, the by-products described in the previous paragraph, for the reaction with alcohols, may be formed; nevertheless, this rarely happens because the water is often in much higher concentration. The amount and nature of the by-products described depend on each specific case, according to the substituents $R^1, R^2$, on the reaction conditions and on the variant of the enzyme that is used. All these by-products are eliminated at the same time as compounds II and III are separated between them by means of a convenient process for each case, such as precipitation or chromatography.

Surprisingly, we have discovered that the addition of a high molar excess of water to the organic medium, not only increases the hydrolysis reaction rate, but that it also changes the enantioselectivity of the catalyst. This fact constitutes a notable improvement of the process and it is part of this invention. In fact, in most cases (using different carbonates of formula II in different solvents), the enzymatic reaction does not take place either in the organic solvent, or when an equimolecular amount of water in relation to the substrate is added. In the few cases in which the enzymatic reaction does have place in the anhydrous solvent with one equivalent of water, the reaction is slow or not very enantioselective. Also, in these cases the addition of the said excess of water enhances the rate and the enantioselectivity, allowing to obtain the product of the reaction in good yield and high enantiomeric riches.

That water effect, in turn, can be modify if it contains salts in dissolution and if the pH is adjusted to a specific value. Moreover, when certain concentration of water and salts is overcome, may happen that the reaction rate and the enantioselectivity decrease again. The optimal values of water amount, salt concentration and pH value depend on the enzyme, on the solvent and on the carbonate II utilised as substrate in each case, and they should be adjusted for each specific case.

Unexpectabily, other organic additives have also a marked effect on the rate and the enantioselectivity of the enzymatic resolution reaction such as, amines or ketones, among others. In some cases the use of these additives is beneficial because they enhances the rate or the enantioselectivity of the reaction, or both at the same time. However, in other cases their effect is negative. In that cases in which its use is favourable, these additives can be used either separately or together with the water or the buffer solution mentioned previously. The optimal nature and concentration for each additive should be determined experimentally for each specific case.

An adequate combination of the water amount, pH, salts concentration and additives, allow to reach high enantioselectivities and consequently, very high enantiomeric excesses and yields.

In other variant of the invention, and depending on the specific reaction conditions, it may happen that the water or buffer added to the organic solvent do not completely mix with the organic solvent, this means that there will be two liquid phases in contact: one organic and other aqueous.

In other variant of the invention, the enzymatic reaction can be performed in aqueous or macro-aqueous medium. In this case it is necessary to add certain amount of organic co-solvent to favour the dissolution of the substrate. However, the amount of co-solvent should not be so high that the biocatalyst results inactivated. As aqueous medium, pure water or, preferably, a buffer solution adjusted to a pH that favour the activity and/or the stability of the enzyme can be used. As co-solvents, solvents, miscible with water, such as acetonitrile or dioxane, among others, can be used. The nature and amount of the co-solvent depend on the carbonate of formula II that is used as substrate, as well as, the variant of the catalyst used, and they have to be experimentally determined in each case by a known method by an expert in the matter.

As enzymatic catalyst hydrolases have to be used. Hydrolases from different sources can be utilised, both from microorganisms and superior organisms. These hydrolases may belong to the proteases, amidases, esterases or lipases groups. Preferably, lipases from *Candida antarctica* are used. These enzymes can be free or immobilized, both in commercial preparations and in others preparations obtained to this end. As it is known, the activity and stability of the enzymes can be modified by immobilization and other known treatments, what can be exploited to improve the process. Preferably, an immobilization preparation compatible with the high concentrations of organic co-solvent, necessary to increase the solubility of the substrate in the medium, should be used. The enzyme, that may be immobilized or not, is preferably in suspension, what facilitates its separation by filtration when the reaction is finished.

The enzymatic resolution of a mixture of enantiomers of the substrate, partially enriched in one of them, is also included in the scope of the invention, following any of the variants of the process described before.

The temperature of the reaction can be between 0 and 100° C., preferably between 20 and 60° C.

Once the corresponding carbonate of formula II, optically enriched, is obtained, it is converted in (+)-zopiclone by reaction with N-methylpiperazine in an inert organic solvent,—for example acetonitrile, tetrahydrofuran, dioxane or acetone, among others—. It is convenient to use a ratio of N-methylpiperazine higher than the equimolecular in relation to the carbonate II, for example 1 to 3, or even higher. Preferably, the reaction should be performed at temperatures below to 15° C. (+)-Zopiclone obtained in this way can be purified by crystallization or chromatography. In a similar way, the racemic carbonates of formula II can be converted into (±)-zopiclona.

Any new intermediate obtained following the process of this invention constitutes a further aspect of the invention.

For a better understanding of the object of the present invention, the following examples are given, which should be taken as not limiting the scope of the invention

EXAMPLES

Example 1

6-(5-chloropyridin-2-yl)-7-oxo-5-(4-nitrophenyloxy-carbonyloxy)-5,6-dihydropyrrolo[3,4b]pyrazine.

p-Nitrophenyl chloroformiate (1.54 g) is slowly added to a suspension of 6-(5-chloropyridin-2-yl)-5-hydroxy-7-oxo-5,6-dihydropyrrolo[3,4b]pyrazine (1.0 g) and pyridine (1.2 ml) in dichloromethane (20 ml) at 0° C. The resulting mixture is stirred for 21 hours at room temperature and then extracted with water and dichloromethane. The organic fraction is dried over sodium sulphate, filtered and concentrated to dryness. The resulting solid is washed with diethyl ether. Yield: 55%.

M.p. 137–139° C.

IR (cm$^{-1}$): 1764, 1746.

$^1$H-NMR (CDCl$_3$), δ (ppm): 8.94 (dd, 2H, CH), 8.58 (d, 1H, CH, $^2J_{HH}$=8.96 Hz), 8.42 (d, 1H, CH, $^3J_{HH}$=2.58 Hz), 8.33 (dd, 2H, CH, $^3J_{HH}$=9.22 Hz), 8.05 (s, 1H, CH), 7.86 (dd, 1H, CH, $^2J_{HH}$=8.96 Hz, $^3J_{HH}$=2.58 Hz), 7.46 (dd, 2H, CH, $^3J_{HH}$=9.22 Hz).

$^{13}$C-NMR (CDCl$_3$), δ (ppm): 163.2 (C=O), 155.8 (C=O), 154.5 (C), 151.8 (C), 149.3 (CH), 148.1 (C), 147.4 (CH), 146.3 (C), 144.6 (C), 139.2 (CH), 129.5 (C), 126.1 (CH), 122.3 (CH), 116.6 (CH), 81.7 (CH).

EM-ESI+: [M+K]=466.0, [M+Na]=450.0.

Example 2

6-(5-chloropyridin-2-yl)-7-oxo-5-(2-propenyloxycarbonyloxy)-5,6-dihydropyrrolo[3,4b]pyrazine.

Isopropenyl chloroformiate (0.54 ml) is slowly added to a suspension of 6-(5-chloropyridin-2-yl)-5-hydroxy-7-oxo-5,6-dihydropyrrolo[3,4b]pyrazine (1.0 g) and pyridine (1 ml) in dichloromethane (30 ml) at 0° C. The resulting mixture is stirred for 6 hours at room temperature and then extracted with water and dichloromethane. The organic fraction is dried over sodium sulphate, filtered and concentrated to dryness. The resulting solid is washed with diethyl ether. Yield: 93%.

M.p. 143–145° C.

IR(cm$^{-1}$): 1772, 1731, 1638, 1619.

$^1$H-NMR (CDCl$_3$), δ (ppm): 8.89 (dd, 2H, 2 CH), 8.52 (d, 1H, CH, $^2J_{HH}$=8.85 Hz), 8.36 (d, 1H, CH, $^3J_{HH}$=2.49 Hz), 8.05 (s, 1H, CH), 7.80 (dd, 1H, CH, $^2J_{HH}$=8.85 Hz, $^3J_{HH}$=2.49 Hz), 4.83 (d, 2H, CH$_2$), 2.01 (s, 3H, CH$_3$).

$^{13}$C-NMR (CDCl$_3$), δ (ppm): 162.4 (C=O), 154.1 (C=O), 152.6 (C), 151.1(C), 148.3 (CH), 148.0 (CH), 147.3 (C), 146.3 (CH), 143.6 (C), 138.1 (CH), 128.3 (C), 115.7 (CH), 102.1 (CH$_2$), 80.3 (CH), 18.8 (CH$_3$).

EM-ESI+: [M+K]=385.0, [M+Na]=369.0

Example 3

5-(1,1-dimethyl-2,2,2-trichloroethyloxycarbonyloxy)-6-(5-chloropyridin-2yl)-7-oxo-5,6-dihydropyrrolo[3,4b]pyrazine 1,1-Dimethyl-2,2,2-trichloroethyl chloroformiate (1.37 g) is slowly added to a suspension of 6-(5-chloropyridin-2-yl)-5-hydroxy-7-oxo-5,6-dihydropyrrolo[3,4b]pyrazine (1.0 g) and pyridine (1.2 ml) in dichloromethane (20 ml) at 0° C. The resulting mixture is stirred for 2 hours at room temperature and then extracted with water and dichloromethane. The organic fraction is dried over sodium sulphate, filtered and concentrated to dryness. The resulting solid is washed with diethyl ether. Yield: 98%.

IR (cm$^{-1}$): 1764, 1738.

$^1$H-NMR (CDCl$_3$), δ (ppm): 9.11 (dd, 2H, 2 CH), 8.64 (d, 1H, CH, $^3J_{HH}$=2.92 Hz), 8.57 (d, 1H, CH, $^2J_{HH}$=8.78 Hz), 8.28 (dd, 1H, CH, $^2J_{HH}$=8.78 Hz, $^3J_{HH}$=2.92), 7.92 (s, 1H, CH), 3.51 (s, 6H, 2 CH$_3$).

$^{13}$C-NMR (CDCl$_3$), δ (ppm): 162.9 (C=O), 154.6 (C=O), 151.1 (C), 148.8 (CH), 148.6 (CH), 148.0 (C), 146.7 (CH), 138.7 (CH), 128.8 (C), 116.3 (CH), 91.5 (C), 80.6 (CH), 21.7 (CH$_3$), 21.4 (CH$_3$).

EM-ESI+: [M+Na]=489.0.

Example 4

6-(5-chloropyridin-2-yl)-7-oxo-5-(2,2,2-trichloroethyloxycarbonyloxy)-5,6-dihydropyrrolo[3,4b]pyrazine.

2,2,2-Trichloroethyl chloroformiate (0.8 ml) is slowly added to a suspension of 6-(5-chloropyridin-2-yl)-5-hydroxy-7-oxo-5,6-dihydropyrrolo[3,4b]pyrazine (1.0 g) and pyridine (1.2 ml) in dichloromethane (30 ml) at 0° C. The resulting mixture is stirred for 5 hours at room temperature and then extracted with water and dichloromethane. The organic fraction is dried over sodium sulphate, filtered and concentrated to dryness. The resulting solid is washed with diethyl ether. Yield: 98%.

M.p.: 201–203° C.

IR(cm$^{-1}$): 1788, 1745.

$^1$H-NMR (CDCl$_3$), δ (ppm): 8.91 (dd, 2H, 2 CH), 8.52 (d, 1H, CH, $^2J_{HH}$=8.77 Hz), 8.34 (d, 1H, CH,$^3J_{HH}$=2.31 Hz), 8.03 (s, 1H, CH), 7.82 (dd, 1H, CH, $^2J_{HH}$=8.72 Hz, $^3J_{HH}$=2.56 Hz), 4.91 (m, 2H, CH$_2$).

$^{13}$C-NMR (CDCl$_3$), δ (ppm): 162.4 (C=O), 153.9 (C=O), 152.5 (C), 148.3 (CH), 147.3 (C), 146.6 (CH), 143.8 (C), 138.3 (CH), 128.6 (C), 115.8 (CH), 93.8 (C), 80.8 (CH), 76.4 (CH$_2$).

EM-ESI+: [M+Na]=458.9.

Example 5

5-(2-chloroethyloxycarbonyloxy)-6-(5-chloropyridin-2-yl)-7-oxo-5,6-dihydropyrrolo[3,4b]pyrazine 2-Chloroethyl chloroformiate (0.8 ml) is slowly added to a suspension of 6-(5-chloropyridin-2-yl)-5-hydroxy-7-oxo-5,6-dihydropyrrolo[3,4b]pyrazine (1.0 g) and pyridine (1.2 ml) in dichloromethane (20 ml) at 0° C. The resulting mixture is stirred for 7hours at room temperature and then extracted with water and dichloromethane. The organic fraction is dried over sodium sulphate, filtered and concentrated to dryness. The resulting solid is washed with diethyl ether. Yield: 98%.

M.p.: 177–178° C.

IR (cm$^{-1}$): 1766, 1741.

$^1$H-NMR (CDCl$_3$), δ (ppm): 8.86 (dd, 2H, 2 CH), 8.52 (d, 1H, CH, $^2J_{HH}$=8.98 Hz), 8.39 (d, 1H, CH, $^3J_{HH}$=2.58 Hz), 7.99 (s, 1H, CH), 7.82 (dd, 1H, CH, $^2J_{HH}$=8.98 Hz, $^3J_{HH}$=2.58), 4.53 (m, 2H, CH$_2$), 3.74 (t, 2H, CH$_2$).

$^{13}$C-NMR (CDCl$_3$), δ (ppm): 162.8 (C=O), 154.6 (C=O), 153.6 (C), 148.6 (CH), 148.6 (CH), 147.8 (C), 147.1 (CH), 144.3 (C), 138.6 (CH), 128.9 (C), 116.3 (CH), 80.8 (CH), 68.5 (CH$_2$), 41.3 (CH$_2$).

EM-ESI+: [M+Na]=391.0.

Example 6

5-(1-chloroethyloxycarbonyloxy)-6-(5-chloropyridin-2-yl)-7-oxo-5,6-dihydropyrrolo[3,4b]pyrazine 1-Chloroethyl chloroformiate (0.8 ml) is slowly added to a suspension of 6-(5-chloropyridin-2-yl)-5-hydroxy-7-oxo-5,6-dihydropyrrolo[3,4b]pyrazine (1.0 g) and pyridine (1.2 ml) in dichloromethane (20 ml) at 0° C. The resulting mixture is stirred for 4 hours at room temperature and then extracted with water and dichloromethane. The organic fraction is dried over sodium sulphate, filtered and concentrated to dryness. The resulting solid is washed with diethyl ether. Yield: 98%. The carbonate obatined is a mixture of diastereoisomers, that can be separated by chromatography.

M.p.: 146–148° C.

IR(cm$^{-1}$): 1760.

$^1$H-NMR (CDCl$_3$), δ (ppm). Diastereoisomer 1: 8.89 (dd, 2H, 2 CH), 8.52 (d, 1H, CH, $^2J_{HH}$=9.09 Hz), 8.39 (d, 1H, CH, $^3J_{HH}$=2.58 Hz), 7.97 (s, 1H, CH), 7.80 (dd, 1H, CH, $^2J_{HH}$=8.98 Hz, $^3J_{HH}$=2.58), 6.55 (q, 1H, CH), 1.82 (d, 3H, CH$_3$, $^3J_{HH}$=5.70 Hz). Diastereoisomer 2: 8.90 (dd, 2H, 2 CH), 8.51 (d, 1H, CH, $^2J_{HH}$=8.88 Hz), 8.36 (d, 1H, CH, $^3J_{HH}$=2.52 Hz), 7.99 (s, 1H, CH), 7.81 (dd, 1H, CH, $^2J_{HH}$=8.88 Hz, $^3J_{HH}$=2.52), 6.54 (q, 1H, CH), 1.84 (d, 3H, CH$_3$, $^3J_{HH}$=5.79 Hz).

$^{13}$C-NMR (CDCl$_3$), δ (ppm): Diastereoisomer 1: 162.4 (C=O), 153.8 (C=O), 151.5 (C), 148.5 (CH), 147.3 (C), 146.6 (CH), 143.8 (C), 138.1 (CH), 128.4 (C), 125.3 (CH), 115.7 (CH), 84.9 (CH), 80.6 (CH), 25.0 (CH$_3$). Diastereoisomer 2: 162.4 (C=O), 153.7 (C=O), 151.1 (C), 148.2 (CH), 147.2 (C), 146.4 (CH), 143.6 (C), 138.1 (CH), 128.4 (C), 125.3 (CH), 115.3 (CH), 84.9 (CH), 80.6 (CH), 24.8 (CH$_3$).

EM-ESI+: [M+K]=407.0, [M+Na]=391.0.

Example 7

5-(chloromethyloxycarbonyloxy)-6-(5-chloropyridin-2-yl)-7-oxo-5,6-dihydropyrrolo[3,4b]pyrazine Chloromethyl chloroformiate (1.0 ml) is slowly added to a suspension of 6-(5-chloropyridin-2-yl)-5-hydroxy-7-oxo-5,6-dihydropyrrolo[3,4b]pyrazine (1.0 g) and pyridine (1.2 ml) in dichloromethane (10 ml) at 0° C. The resulting mixture is stirred for 17 hours at room temperature and then extracted with water and dichloromethane. The organic fraction is dried over sodium sulphate, filtered and concentrated to dryness. The resulting solid is washed with diethyl ether. Yield: 86%.

M.p. 135–137° C.

IR (cm$^{-1}$): 1748, 1804.

$^1$H-NMR (CDCl$_3$), δ (ppm): 8.89 (dd, 2H, 2 CH), 8.50 (d, 1H, CH, $^2J_{HH}$=8.85 Hz), 8.37 (d, 1H, CH, $^3J_{HH}$=8.85 Hz), 7.97 (s, 1H, CH), 7.80 (dd, 1H, CH, $^2J_{HH}$=2.52 Hz, $^3J_{HH}$=8.88 Hz), 5.81 (dd, 2H, CH$_2$).

$^{13}$C-NMR (CDCl$_3$), δ (ppm): 163.0 (C=O), 154.5 (C=O), 152.8 (C), 149.1 (CH), 148.0 (C), 147.4 (CH), 144.5 (C), 139.0 (CH), 129.2 (C), 116.3 (CH), 81.6 (CH), 73.2 (CH$_2$).

EM-ESI+: [M+Na]=376.9, [M+H]=355.0.

Example 8

6-(5-chloropyridin-2-yl)-7-oxo-5-(N-succinimidyloxycarbonyloxi)-5,6-dihydropyrrolo[3,4b]pyrazine Disuccinimidyl carbonate (2.0 g) and triethyl amine (2.1 ml) are added to a suspension of 6-(5-chloropyridin-2-yl)-5-hydroxy-7-oxo-5,6-dihydropyrrolo[3,4b]pyrazine (1.0 g) and pyridine (1.2 ml) in anhydrous acetonitrile (20 ml) at 0° C. The resulting mixture is stirred for 18 hours at room temperature and then extracted with water and dichloromethane. The organic fraction is dried over sodium sulphate, filtered and concentrated to dryness. The resulting solid is washed with diethyl ether. Yield: 40%. M.p. 180–183° C. IR (cm$^{-1}$): 1739.

Example 9

Immobilization of the Enzyme

The commercial lipase of *Candida antarctica* B is purified by interfacial adsorption on octyl-agarose derivatives and subsequent desorption with Triton X100. This purified lipase is diluted 10-fold. Then 12 mg of protein (according to Bradford method) per ml of different supports, which offer covalent bounding (glyoxyl-agarose, glutaraldehyde-agarose), ionic adsorption (poliethylenimine) or interfacial adsorption (octyl-agarose and epoxide-acrylic decaoctyl-resin) are mixed up. The tests of desorption and inactivation in water, in the presence of increasing amounts of dioxane at different temperatures, showed that the interfacial adsorbed derivative absorbed on epoxide-acrylic decaoctyl-resin is the most stable and that the one that allow wider range of working conditions. The epoxide-acrylic decaoctyl-resin also possesses higher mechanical strength than the others studied, remaining intact after having been subjected to mechanical stirring for a week.

Example 10

Synthesis of (+)-zopiclone.

N-Methylpiperazine (0.48 ml, 4.2 mmol) is added to a solution of the (S)-5-(chloromethyloxycarbonyloxy)-6-(5-chloropyridin-2-yl)-7-oxo-5,6-dihydropyrrolo[3,4b]pyrazine (0.5 g, 1.4 mmol) in anhydrous acetone (6 ml) under nitrogen at 0° C. The resulting mixture is allowed to warm at 15° C., stirred for 2 hours and then the solvent is evaporated under reduced pressure and the crude residue is purified by flash chromatography on silica gel using acetone as eluent. Yield: 90%, ee>99%, $[\alpha]_D^{18}$=+176 (c 1.1, HCCl$_3$).

Example 11

Enzymatic Resolution of the Intermediate II (R$^1$=—CH$_2$—Cl).

2 M Phosphate buffer (pH 7, 0.2 ml) and immobilised *Candida antarctica* lipase B (0.2 g) are added to a solution of 5-(chloromethyloxycarbonyloxy)-6-(5-chloropyridin-2-yl)-7-oxo-5,6-dihydropyrrolo[3,4b]pyrazine (0.2 g) and pyrazine (20 mg) in toluene (40 ml). The resulting mixture is shaken at 250 rpm in a rotatory shaker at 60° C. for 100 hours. When the reaction is finished, the enzyme is filtered and the remaining substrate, (S)-5-(chloromethyloxycarbonyloxy)-6-(5-chloropyridin-2-yl)-7-oxo-5,6-dihydropyrrolo[3,4b]pyrazine, is purified by flash chromatography. Yield: 49%, ee>99%, $[\alpha]_D^{18}$=+94 (c 1.1, HCCl$_3$), m.p. 157–159° C.

Example 12

Enzymatic Resolution of the Intermediate II (R$^1$=—CH$_2$—Cl).

2 M Phosphate buffer (pH 7, 0.2 ml) and immobilised *Candida antarctica* lipase B (0.2 g) are added to a solution of 5-(chloromethyloxycarbonyloxy)-6-(5-chloropyridin-2-yl)-7-oxo-5,6-dihydropyrrolo[3,4b]pyrazine (0.2 g) in toluene (40 ml). The resulting mixture is shaken at 250 rpm in a rotatory shaker at 60° C. for 100 hours. When the reaction is finished, the enzyme is filtered and the remaining substrate, (S)-5-(chloromethyloxycarbonyloxy)-6-(5-chloropyridin-2-yl)-7-oxo-5,6-dihydropyrrolo[3,4b]pyrazine, is purified by flash chromatography. Yield: 45%, ee 96%, m.p. 154–156° C. The enantiomeric excess and therefore, the enantioselectivity are lower than in example 12, where pyrazine is added to the reaction medium.

Example 13

Enzymatic Resolution of the Intermediate II (R$^1$=—CH$_2$CH$_2$—Cl).

A solution 6 mM of 5-(2-chloroethyloxycarbonyloxy)-6-(5-chloropyridin-2-yl)-7-oxo-5,6-dihydropyrrolo[3,4b] pyrazine in a mixture 1:1 of dioxane and 10 mM phosphate (pH 7) is prepared. 2.0 g of *Candida antarctica* lipase B absorbed on epoxyacrylic support activated with decaoctyl groups are added to that solution. The resulting mixture is incubated at 37° C. and 250 rpm. After 140 hours a conversion of 51% is reached, being the enantioselectivity E>100, what corresponds to an enantiomeric excess ee>99%.

What is claimed is:

1. A compound of formula II which is optically enriched, wherein R$^1$ is a haloalkyl group

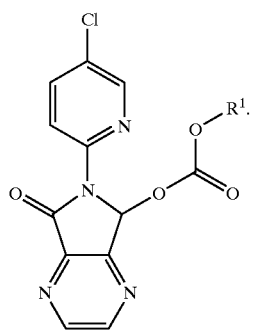

II

2. A compound in accordance with claim 1 having an enantiomeric excess greater than 90%.

3. A process for preparing a carbonate of claim 1 which is enantiomerically enriched which comprises the steps of
(a) stereospecifically reacting a mixture of both enantiomers of a compound of formula II with a nucleophile in the presence of an enzyme in accordance with the following reaction wherein $R^1$ is a "haloalkyl" and $R^2$—XH is a nucleophile selected from the group consisting of water, methanol, ethanol, 2-propanol and butanol

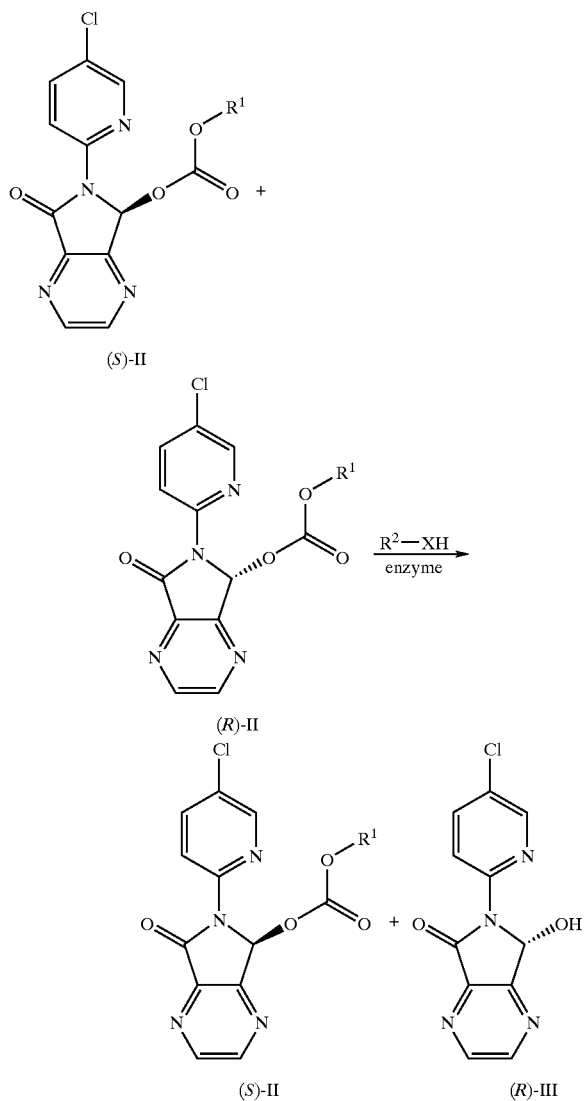

(b) terminating the reaction at a determined conversion less than 100%, and
(c) separating the compound of formula (R)-III from compound (S)-II wherein the enzyme is an enzyme of the lipase class.

4. A process in accordance with claim 3 wherein the reaction is conducted in an organic solvent or in a mixture of two or more solvents.

5. A process in accordance with claim 3 wherein the reaction is conducted in a biphasic mixture of an aqueous phase and an organic solvent that is miscible with the aqueous medium.

6. A process in accordance with claim 4 wherein at least one of said organic solvents is selected from the group consisting of dioxane, tetrahydrofuran, tert-butylmethylether, di-isopropylether, diethylene, toluene, hexane, acetonitrile, acetone, 2-propanol, 2-methyl-2-propanol, chloroform and dichloromethane.

7. A process in accordance with claim 4 wherein the reaction medium comprises between 40% and 60% of an organic solvent miscible with water.

8. A process in accordance with claim 7 wherein the organic solvent is dioxane.

9. A process in accordance with claim 7 wherein the organic solvent is acetonitrile.

10. A process in accordance with claim 4 wherein $R^1$ is 2-chloroethyl.

11. A process in accordance with claim 4 wherein $R^1$ is chloromethyl.

12. A process in accordance with claim 3 wherein the enzyme is the fraction B from the lipase of *Candida antarctica*.

13. A process in accordance with claim 4 wherein the reaction medium includes additives which modify the activity or enantioselectivity of the enzyme.

14. A process in accordance with claim 13 wherein the additives are aliphatic amines.

15. A process in accordance with claim 13 wherein the additive is pyrazine.

16. A process in accordance with claim 4 wherein compound II recovered from the enzymatic reaction has an absolute configuration (S).

17. A process for the preparation of an optionally enriched zopiclone which comprises reacting N-methylpiperazine with an optically enriched carbonate obtained in accordance with claim 3.

18. A process for the preparation of optically enriched (S)-zopiclone which comprises reacting N-methylpiperazine with an optically enriched carbonate having an absolute configuration (S) obtained in accordance with claim 3.

* * * * *